United States Patent [19]

Grubbs et al.

[11] Patent Number: 5,342,909
[45] Date of Patent: Aug. 30, 1994

[54] RUTHENIUM AND OSMIUM METAL CARBENE COMPLEXES FOR OLEFIN METATHESIS POLYMERIZATION

[75] Inventors: Robert H. Grubbs, South Pasadena, Calif.; Lynda K. Johnson, Carrboro, N.C.; Sonbinh T. Nguyen, Pasadena, Calif.

[73] Assignee: California Institute of Technology, Pasadena, Calif.

[21] Appl. No.: 106,292

[22] Filed: Aug. 13, 1993

Related U.S. Application Data

[62] Division of Ser. No. 863,606, Apr. 3, 1992.

[51] Int. Cl.[5] .......................... C08F 4/80; C08F 32/04; C08F 32/08; C07F 15/00
[52] U.S. Cl. ..................................... 526/171; 526/90; 526/91; 526/92; 526/93; 526/170; 526/172; 526/183; 526/280; 526/281; 526/283; 556/136
[58] Field of Search .................. 526/170, 171, 283, 93; 556/136

[56] References Cited

U.S. PATENT DOCUMENTS

| | | | |
|---|---|---|---|
| 4,883,851 | 11/1989 | Grubbs et al. | 526/268 |
| 4,945,135 | 7/1990 | Grubbs et al. | 525/338 |
| 4,945,141 | 7/1990 | Grubbs et al. | 526/90 |
| 4,945,144 | 7/1990 | Grubbs et al. | 526/268 |

OTHER PUBLICATIONS

J. P. Collman et al., J. Am. Chem. Soc. 1986, 108, 1332–1333.
K. J. Ivin, "Olefin Metathesis", 34–36, (1983) Academic Press (London).
Bunell et al., "Synthesis and Reactions of Ru(=CH$_2$) Cl(NO)(PPh$_3$)$_2$, A Stable Terminal Methylene Complex and the Crystal Structure of Ru(CH$_2$PPh$_3$)$_2$(-n$^2$-C$_2$F$_4$)Cl(NO)(PPh$_3$)", J. Chem. Soc., Dalton Trans., 1991.
Iroin, "Olefin Metathesis", 1983.
McGrath et al., "Aqueous Ring-Opening Metathesis Polymerization of 7-Oxanorbornene Derivatives Using Ruthenium Catalysts", 1990.
Novak et al., "Catalytic Organometalic Chemistry in Water: The Aqueous Ring-Opening Metathesis Polymerization of 7-Oxanorbornene Derivatives", 1988, JACS, vol. 110.
Novak et al., "The Ring Opening Metathesis Polymerization of 7-Oxabicyclo [2.2.2]hept-5-ene Derivatives: A New Acyclic Polymeric Ionophere", 1988, JACS, vol. 110.
Hillmyer et al., "The Aqueous Ring-Opening Metathesis Polymerization of exo-N-Methyl-7-oxabicyclo [2.2.1] hept-5-ene-2, 3-dicarbonximide" 1991.
Carter et al., "Review of the Chemistry of Cyclopropane Compounds", Apr. 20, 1964, pp. 34–36.
Schmidbaur et al., "Ylide Chemistry: An Account of Structural, Conformational and Redox Investigations" 1983.
"Metathesis of Functionalized Olefin", J. of Molecules Catalysis, 15 (1982), pp. 35–45.
Bruce et al., "Cyclopentadienyl-Ruthenium and -osmium Chemistry. Some Reactions of Substituted Vinylidene Complexes," J. Organometallic Chem. 171:C5–C8 (1979).
M. H. L. Green et al., "Carbene Complexes of Iron, Molybdenum, and Ruthenium: A New Route to Metal-Carbene Derivatives," J. Chem. Soc., (A) 794–797 (1971).
H. Le Bozec et al., "A New Route to Vinylcarbene Metal Complexes in One Step from 2-Propyn-1-ols and Arene Ruthenium(∥) Derivatives," J. Chem. Soc. Chem. Comm. 219–221.
Nguyen et al., "Ring-Opening Metathesis Polymerization (ROMP) of Norbornene by a Group VIII Carbene Complex in Protic Media," J. Am. Chem. Soc. 114:3974–3975 (1992).
Grundy et al., "Migratory-Insertion Reactions of Osmium (II) Ethyl Complexes Derived From a Osmium (0) Ethylene Complex," J. Organometallic Chem. 216:255–262 (1981).
Grundy et al., "Propionyl Complexes of Ruthenium Derived From the Reaction of Ethylene with RuHCl-(CO)$_2$(PPh$_3$)$_2$, " J. Organometallic Chem. 265:77–85 (1984).
Collman et al., J. Am. Chem. Soc., Vol. 108, pp. 1332–1333 (1986).

Primary Examiner—Fred Zitomer
Attorney, Agent, or Firm—Limbach & Limbach

[57] ABSTRACT

Processes for the synthesis of several new carbene compounds of ruthenium and osmium are provided. These novel complexes function as stable, well-defined catalysts for the metathesis polymerization of cyclic olefins.

5 Claims, No Drawings

RUTHENIUM AND OSMIUM METAL CARBENE COMPLEXES FOR OLEFIN METATHESIS POLYMERIZATION

This is a divisional of application Ser. No. 07/863,606, filed Apr. 3, 1992, pending.

BACKGROUND OF THE INVENTION

This invention relates to new ruthenium and osmium metal carbene complex compounds and their utility in an improved catalytic process for olefin metathesis polymerization.

During the past two decades, research efforts have enabled an in depth understanding of the olefin metathesis reaction as catalyzed by early transition metal complexes. In contrast, the nature of the intermediates and the reaction mechanism for Group VIII transition metal catalysts has remained elusive. In particular, the oxidation states and ligation of the ruthenium and osmium metathesis intermediates are not known. Furthermore, the discrete ruthenium and osmium carbene complexes isolated to date do not exhibit metathesis activity.

Many ruthenium and osmium metal carbenes have been reported in the literature (for example, see Burrell, A. K., Clark, G. R., Rickard, C. E. F., Roper, W. R., Wright, A. H., *J. Chem. Soc.*, Dalton Trans., 1991, Issue 1, pp. 609-614).

SUMMARY OF THE INVENTION

The present invention involves a reaction of a ruthenium or osmium compound with either a cyclopropene or a phosphorane to produce well-defined carbene compounds which can be called carbene complexes and which can catalyze the polymerization of cyclic olefin via ring-opening metathesis.

The carbene compounds of the present invention are the only Ru and Os carbene complexes known to date in which the metal is formally in the +2 oxidation state, has an electron count of 16, and is pentacoordinate. The compounds claimed herein are active catalysts for ring-opening metathesis polymerization ("ROMP"). Most metathesis catalysts presently known are poisoned by functional groups and are, therefore, incapable of catalyzing metathesis polymerization reactions in protic or aqueous solvent systems.

Thus, the present invention pertains to compounds of the formula

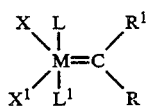

I wherein:
M is Os or Ru;
R and $R^1$ are independently selected from hydrogen; $C_2$–$C_{20}$ alkenyl, $C_2$–$C_{20}$ alkynyl, $C_1$–$C_{20}$ alkyl, aryl, $C_1$–$C_{20}$ carboxylate, $C_1$–$C_{20}$ alkoxy, $C_2$–$C_{20}$ alkenyloxy, $C_2$–$C_{20}$ alkynyloxy, aryloxy, $C_2$–$C_{20}$ alkoxycarbonyl, $C_1$–$C_{20}$ alkylthio, $C_1$–$C_{20}$ alkylsulfonyl or $C_1$–$C_{20}$ alkylsulfinyl; each optionally substituted with $C_1$–$C_5$ alkyl, halogen, $C_1$–$C_5$ alkoxy or with a phenyl group optionally substituted with halogen, $C_1$–$C_5$ alkyl or $C_1$–$C_5$ alkoxy;
X and $X^1$ are independently selected from any anionic ligand; and
L and $L^1$ are independently selected from any neutral electron donor.

In one embodiment of these compounds, they can be in the form wherein 2, 3, or 4 of the moieties X, $X^1$, L, and $L^1$ can be taken together to form a chelating multidentate ligand. In one aspect of this embodiment, X, L, and $L^1$ can be taken together to form a cyclopentadienyl, indenyl, or fluorenyl moiety.

The present invention also pertains to a method of preparing the aforementioned ruthenium and osmium compounds comprising reacting a compound of the formula $(XX^1ML_nL^1{}_m)_p$, in the presence of solvent, with a cyclopropene of the formula

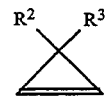

wherein:
M, X, $X^1$, L, and $L^1$ have the same meaning as indicated above;
n and m are independently 0–4, provided n+m=2, 3 or 4;
p is an integer equal to or greater than 1; and
$R^2$ and $R^3$ are independently selected from hydrogen; $C_1$–$C_{18}$ alkyl, $C_2$–$C_{18}$ alkenyl, $C_2$–$C_{18}$ alkynyl, $C_2$–$C_{18}$ alkoxycarbonyl, aryl, $C_1$–$C_{18}$ carboxylate, $C_1$–$C_{18}$ alkenyloxy, $C_2$–$C_{18}$ alkynyloxy, $C_1$–$C_{18}$ alkoxy, aryloxy, $C_1$–$C_{18}$ alkylthio, $C_1$–$C_{18}$ alkylsulfonyl or $C_1$–$C_{18}$ alkylsulfinyl; each optionally substituted with $C_1$–$C_5$ alkyl, halogen, $C_1$–$C_5$ alkoxy or with a phenyl group optionally substituted with halogen, $C_1$–$C_5$ alkyl or $C_1$–$C_5$ alkoxy.

In one embodiment of the process, X, L, and $L^1$ are taken together to form a moiety selected from the group consisting of cyclopentadienyl, indenyl or fluorenyl, each optionally substituted with hydrogen; $C_2$–$C_{20}$ alkenyl, $C_2$–$C_{20}$ alkynyl, $C_1$–$C_{20}$ alkyl, aryl, $C_1$–$C_{20}$ carboxylate, $C_1$–$C_{20}$ alkoxy, $C_2$–$C_{20}$ alkenyloxy, $C_2$–$C_{20}$ alkynyloxy, aryloxy, $C_2$–$C_{20}$ alkoxycarbonyl, $C_1$–$C_{20}$ alkylthio, $C_1$–$C_{20}$ alkylsulfonyl, $C_1$–$C_{20}$ alkylsulfinyl; each optionally substituted with $C_1$–$C_5$ alkyl, halogen, $C_1$–$C_5$ alkoxy or with a phenyl group optionally substituted with halogen, $C_1$–$C_5$ alkyl or $C_1$–$C_5$ alkoxy.

A still further method of preparing the compounds of this invention comprises reacting compound of the formula $(XX^1ML_nL^1{}_m)_p$ in the presence of solvent with phosphorane of the formula

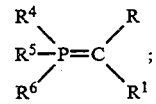

wherein:
M, X, $X^1$, L, $L^1$, n, m, p, R, and $R^1$ have the same meaning as indicated above; and
$R^4$, $R^5$ and $R^6$ are independently selected from aryl, $C_1$–$C_6$ alkyl, $C_1$–$C_6$ alkoxy or phenoxy, each optionally substituted with halogen, $C_1$–$C_3$ alkyl, $C_1$–$C_3$ alkoxy, or with a phenyl group optionally substituted with halogen, $C_1$–$C_5$ alkyl or $C_1$–$C_5$ alkoxy.

Another embodiment of the invention comprises preparing compounds of Formulae II and III

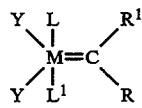

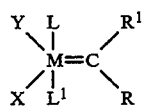

from compound of Formula I

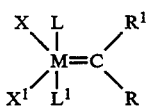

comprising reacting said compound of Formula I, in the presence of solvent, with compound of the formula M¹Y wherein:

M, R, R¹ X, X¹ L, and L¹ have the same meaning as indicated above, and wherein:

(1) M¹ is Li, Na or K, and Y is $C_1$-$C_{10}$ alkoxide or arylalkoxide each optionally substituted with $C_1$-$C_{10}$ alkyl or halogen, diaryloxide; or (2) M¹ is Na or Ag, and Y is $ClO_4$, $PF_6$, $BF_4$, $SbF_6$, halogen, B(aryl)$_4$, $C_1$-$C_{10}$ alkyl sulfonate or aryl sulfonate.

Another embodiment of the present invention is a method of preparing compounds of structures of Formulae IV and V

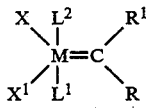

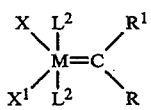

from compound of Formula I

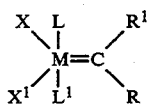

comprising reacting said compound I, in the presence of solvent, with L² wherein:

M, R, R¹ X, and X¹ have the same meaning as indicated above; and

L, L¹, and L² are independently selected from any neutral electron donor.

The compounds of Formulae II, III, IV, and V are species of, i.e., fall within, the scope of compounds of Formula I. In other words, certain compounds of Formula I are used to form by ligand exchange other compounds of Formula I. In this case, X and X¹ in Formula I are other than the Y in Formulae II and III that replaces X. Similarly, L and L¹ in Formula I are other than the L² in Formulae IV and V. If any 2, 3, or 4 of X, X¹, L, and L¹ form a multidentate ligand of Formula I, only the remaining ligand moieties would be available for ligand replacement.

Still another embodiment of the present invention involves the use of compound I as a catalyst for polymerizing cyclic olefin. More specifically, this embodiment comprises metathesis polymerization of a polymerizable cyclic olefin in the presence of catalyst of the formula

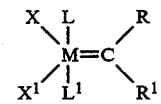

in the presence of solvent, wherein:

M, R, R¹ X X¹ L and L¹ have the same meaning as indicated above.

The reference above to X, X¹, L, and L¹ having the same meaning as indicated above refers to these moieties individually and taken together to form a multidentate ligand as described above.

DETAILED DESCRIPTION

The ruthenium and osmium metal complexes of the present invention are useful as catalysts in ring-opening metathesis polymerization, particularly in the living polymerization of strained cyclic olefins. Although all the criteria for a living polymer have not been completely established, the term living is used in the sense that the propagating moiety is stable and will continue to polymerize additional aliquots of monomer for a period after the original amount of monomer has been consumed. Aspects of this invention include the metal complex compounds, methods for their preparation, as well as their use as catalysts in the ROMP reaction. Uses for the resultant polymer are well documented in the book, *Olefin Metathesis*, by K. J. Ivin, Academic Press, Harcourt Brace Jovanovich Publishers (1983).

The intermediate compounds $(XX^1ML_nL^1_m)_p$ are either available commercially or can be prepared by standard known methods.

The phosphorane and cyclopropene reactants used in the present invention may be prepared in accordance with the following respective references. Schmidbaur, H. et al., *Phosphorus and Sulfur*, Vol. 18, pp. 167–170 (1983); Carter, F. L., Frampton, V. L., *Chemical Reviews*, Vol. 64, No. 5 (1964).

In the compounds of Formula I:

alkyl can include methyl, ethyl, n-propyl, i-propyl, or the several butyl, pentyl or hexyl isomers;

alkenyl can include 1-propenyl, 2-propenyl; 3-propenyl and the different butenyl, pentenyl and hexenyl isomers, 1,3-hexadienyl and 2, 4,6-heptatrienyl, and cycloalkenyl;

alkenyloxy can include $H_2C=CHCH_2O$, $(CH_3)_2C=CHCH_2O$, $(CH_3)CH=CHCH_2O$, $(CH_3)CH=C(CH_3)CH_2O$ and $CH_2=CHCH_2CH_2O$;

alkynyl can include ethynyl, 1-propynyl, 3-propynyl and the several butynyl, pentynyl and hexynyl isomers, 2,7-octadiynyl and 2,5,8-decatriynyl;

alkynyloxy can include $HC\equiv CCH_2O$, $CH_3C\equiv CCH_2O$ and $CH_3C\equiv CCH_2OCH_2O$;

alkylthio can include, methylthio, ethylthio, and the several propylthio, butylthio, pentylthio and hexylthio isomers;

alkylsulfonyl can include $CH_3SO_2$, $CH_3CH_2SO_2$, $CH_3CH_2CH_2SO_2$, $(CH_3)_2CHSO_2$ and the different butylsulfonyl, pentylsulfonyl and hexylsulfonyl isomers;

alkylsulfinyl can include $CH_3SO$, $CH_3CH_2SO$, $CH_3CH_2CH_2SO$, $(CH_3)_2CHSO$ and the different butylsulfinyl, pentylsulfinyl and hexylsulfinyl isomers;

carboxylate can include $CH_3CO_2CH_3CH_2CO_2$, $C_6H_5CO_2$, $(C_6H_5)CH_2CO_2$;

aryl can include phenyl, p-tolyl and p-fluorophenyl;

alkoxide can include methoxide, t-butoxide, and phenoxide;

diketonates can include acetylacetonate and 2,4-hexanedionate;

sulfonate can include trifluoromethanesulfonate, tosylate, and mesylate;

phosphine can include trimethylphosphine, triphenylphosphine, and methyldiphenylphosphine;

phosphite can include trimethylphosphite, triphenylphosphite, and methyldiphenylphosphite;

phosphinite can include triphenylphosphinite, and methyldiphenylphosphinite;

arsine can include triphenylarsine and trimethylarsine;

stibine can include triphenylstibine and trimethylstibine;

amine can include trimethylamine, triethylamine and dimethylamine;

ether can include $(CH_3)_3CCH_2OCH_2CH_3$, THF, $(CH_3)_3COC(CH_3)_3$, $CH_3OCH_2CH_2OCH_3$, and $CH_3OC_6H_5$;

thioether can include $CH_3SCH_3$, $C_6H_5SCH_3$, $CH_3OCH_2CH_2SCH_3$, and tetrahydrothiophene;

amide can include $HC(=O)N(CH_3)_2$ and $(CH_3)C(=O)N(CH_3)_2$;

sulfoxide can include $CH_3S(=O)CH_3$, $(C_6H_5)_2SO$;

alkoxy can include methoxy, ethoxy, n-propyloxy, isopropyloxy and the different butoxy, pentoxy and hexyloxy isomers, cycloalkoxy can include cyclopentyloxy and cyclohexyloxy;

cycloalkyl can include cyclopropyl, cyclobutyl, cyclopentyl, and cyclohexyl; and cycloalkenyl can include cyclopentenyl and cyclohexenyl.

The term "halogen" or "halide", either alone or in compound words such as "haloalkyl", denotes fluorine, chlorine, bromine or iodine.

Alkoxyalkyl can include $CH_3OCH_2$, $CH_3OCH_2CH_2$, $CH_3CH_2OCH_2CH_3CH_2CH_2OCH_2$ and $CH_3CH_2OCH_2CH_2$; and alkoxycarbonyl can include $CH_3OC(=O)$, $CH_3CH_2OC(=O)$, $CH_3CH_2CH_2OC(=O)$, $(CH_3)_2CHOC(=O)$ and the different butoxy-, pentoxy- or hexyloxycarbonyl isomers.

A neutral electron donor is any ligand which, when removed from a metal center in its closed shell electron configuration, has a neutral charge, i.e., is a Lewis base.

An anionic ligand is any ligand which when removed from a metal center in its closed shell electron configuration has a negative charge. The critical feature of the carbene compounds of this invention is the presence of the ruthenium or osmium in the +2 oxidation state, an electron count of 16 and pentacoordination. A wide variety of ligand moieties X, $X^1$, L, and $L^1$ can be present and the carbene compound will still exhibit its catalytic activity.

A preferred embodiment of the compounds of the present invention is:

A compound of the invention of Formula I wherein:
R and $R^1$ are independently selected from hydrogen, vinyl, $C_1$–$C_{10}$ alkyl, aryl, $C_1$–$C_{10}$ carboxylate, $C_2$–$C_{10}$ alkoxycarbonyl, $C_1$–$C_{10}$ alkoxy, aryloxy, each optionally substituted with $C_1$–$C_5$ alkyl, halogen, $C_1$–$C_5$ alkoxy or with a phenyl group optionally substituted with halogen, $C_1$–$C_5$ alkyl or $C_1$–$C_5$ alkoxy;

X and $X^1$ are independently selected from halogen, hydrogen, or $C_1$–$C_{20}$ alkyl, aryl, $C_1$–$C_{20}$ alkoxide, aryloxide, $C_2$–$C_{20}$ alkoxycarbonyl, arylcarboxylate, $C_1$–$C_{20}$ carboxylate, aryl or $C_1$–$C_{20}$ alkylsulfonate, $C_1$–$C_{20}$ alkylthio, $C_1$–$C_{20}$ alkylsulfonyl, $C_1$–$C_{20}$ alkylsulfinyl, each optionally substituted with $C_1$–$C_5$ alkyl, halogen, $C_1$–$C_5$ alkoxy or with a phenyl group optionally substituted with halogen, $C_1$–$C_5$ alkyl or $C_1$–$C_5$ alkoxy; and L and $L^1$ are independently selected from phosphine, sulfonated phosphine, phosphite, phosphinite, phosphonite, arsine, stibine, ether, amine, amide, sulfoxide, carbonyl, nitrosyl, pyridine or thioether.

A more preferred embodiment of Formula I comprises:

A compound of the invention wherein:
R and $R^1$ are independently selected from hydrogen; vinyl, $C_1$–$C_5$ alkyl, phenyl, $C_2$–$C_5$ alkoxycarbonyl, $C_1$–$C_5$ carboxylate, $C_1$–$C_5$ alkoxy, phenoxy; each optionally substituted with $C_1$–$C_5$ alkyl, halogen, $C_1$–$C_5$ alkoxy or a phenyl group optionally substituted with halogen, $C_1$–$C_5$ alkyl or $C_1$–$C_5$ alkoxy;

X and $X^1$ are independently selected from Cl, Br, H, or benzoate, $C_1$–$C_5$ carboxylate, $C_1$–$C_5$ alkyl, phenoxy, $C_1$–$C_5$ alkoxy, $C_1$–$C_5$ alkylthio, aryl, and $C_1$–$C_5$ alkyl sulfonate; each optionally substituted with $C_1$–$C_5$ alkyl or a phenyl group optionally substituted with halogen, $C_1$–$C_5$ alkyl or $C_1$–$C_5$ alkoxy;

L and $L^1$ are independently selected from aryl or $C_1$–$C_{10}$ alkylphosphine, aryl- or $C_1$–$C_{10}$ alkylsulfonated phosphine, aryl- or $C_1$–$C_{10}$ alkylphosphinite, aryl- or $C_1$–C10 alkylphosphonite, aryl- or $C_1$–$C_{10}$ alkylphosphite, aryl- or $C_1$–$C_{10}$ alkylarsine, aryl- or $C_1$–$C_{10}$ alkylamine, pyridine, aryl- or $C_1$–$C_{10}$ alkyl sulfoxide, aryl- or $C_1$–$C_{10}$ alkylether, or aryl- or $C_1$–$C_{10}$ alkylamide, each optionally substituted with a phenyl group optionally substituted with halogen, $C_1$–$C_5$ alkyl or $C_1$–$C_5$ alkoxy.

A further preferred embodiment of Formula I comprises:

A compound of the present invention wherein:
R and $R^1$ are independently vinyl, H, Me, Ph;

X and $X^1$ are independently Cl, $CF_3CO_2$, $CH_3CO_2$, $CH_3CO_2$ $CFH_2CO_2$, $(CH_3)_3CO$, $(CF_3)_2(CH_3)CO$, $(CF_3)(CH_3)_2CO$, PhO, MeO, EtO, tosylate, mesylate, or trifluoromethanesulfonate; and L and $L^1$ are independently $PMe_3$, $PPh_3$, $P(p-Tol)_3$, $P(o-Tol)_3$, $PMePh_2$, $PPhMe_2$, $P(CF_3)_3$, $P(p-FC_6H_4)_3$, pyridine, $P(P-CF_3C_6H_4)_3$, (p-F)pyridine, (p-$CF_3$)pyridine, P $(C_6H_4-SO_3Na)_3$ or $P(CH_2C_6H_4-SO_3Na)_3$.

For any of the foregoing described preferred groups of compounds, any 2, 3, or 4 of X, $X^1$, L, $L^1$ can be taken together to form a chelating multidentate ligand. Examples of bidentate ligands include, but are not limited to, bisphosphines, dialkoxides, alkyldiketonates, and aryldiketonates. Specific examples include $Ph_2PCH_2CH_2PPh_2$, $Ph_2AsCH_2CH_2AsPh_2$, $Ph_2PCH_2CH_2C(CF_3)O—$, binaphtholate dianions, pinacolate dianions, Me$_2$P(CH$_2$)$_2$PMe$_2$ and $^-$OC(CH$_3$)$_2$(CH$_3$)$_2$CO$^-$. Preferred bidentate ligands are Ph$_2$PCH$_2$CH$_2$PPh$_2$ and Me$_2$PCH$_2$CH$_2$PMe$_2$. Tridentate ligands include, but are not limited to, (CH$_3$)$_2$NCH$_2$CH$_2$P(Ph)CH$_2$CH$_2$N(CH$_3$)$_2$. Other preferred tridentate ligands are those in which X, L, and L$^1$ are taken together to be cyclopentadienyl, indenyl or fluorenyl, each optionally substituted with C$_2$-C$_{20}$ alkenyl, C$_2$-C$_{20}$ alkynyl, C$_1$-C$_{20}$ alkyl, aryl, C$_1$-C$_{20}$ carboxylate, C$_1$-C$_{20}$ alkoxy, C$_2$-C$_{20}$ alkenyloxy, C$_2$-C$_{20}$ alkynyloxy, aryloxy, C$_2$-C$_{20}$ alkoxycarbonyl, C$_1$-C$_{20}$ alkylthio, C$_1$-C$_{20}$ alkylsulfonyl, C$_1$-C$_{20}$ alkylsulfinyl, each optionally substituted with C$_1$-C$_5$ alkyl, halogen, C$_1$-C$_5$ alkoxy or with a phenyl group optionally substituted with halogen, C$_1$-C$_5$ alkyl or C$_1$-C$_5$ alkoxy. More preferably in compounds of this type, X, L, and L$^1$ are taken together to be cyclopentadienyl or indenyl, each optionally substituted with hydrogen; vinyl, C$_1$-C$_{10}$ alkyl, aryl, C$_1$-C$_{10}$ carboxylate, C$_2$-C$_{10}$ alkoxycarbonyl, C$_1$-C$_{10}$ alkoxy, aryloxy, each optionally substituted with C$_1$-C$_5$ alkyl, halogen, C$_1$-C$_5$ alkoxy or with a phenyl group optionally substituted with halogen, C$_1$-C$_5$ alkyl or C$_1$-C$_5$ alkoxy. Most preferably, X, L, and L$^1$ are taken together to be cyclopentadienyl, optionally substituted with vinyl, hydrogen, Me or Ph. Tetradentate ligands include, but are not limited to O$_2$C(CH$_2$)$_2$P(Ph)(CH$_2$)$_2$P(Ph)(CH$_2$)$_2$CO$_2$, phthalocyanines, and porphyrins.

The most preferred carbene compounds of the present invention include:

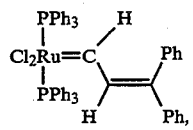

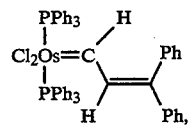

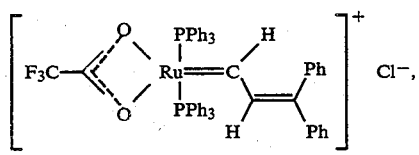

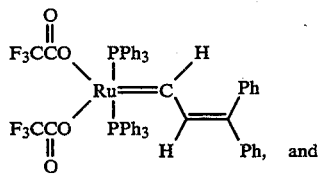

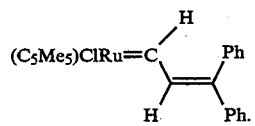

The compounds of the present invention can be prepared in several different ways, each of which is described below.

The most general method for preparing the compounds of this invention comprises reacting (XX$^1$ML$_n$L$^1$$_m$)$_p$ with a cyclopropene or phosphorane in the presence of a solvent to produce a carbene complex, as shown in the equations.

REACTION EQUATIONS

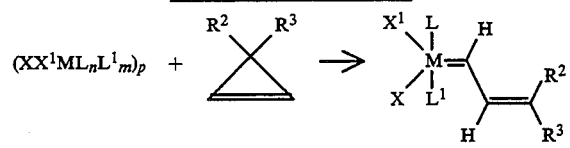

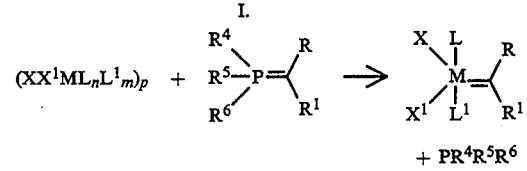

wherein:

M, X, X$^1$, L, L$^1$, n, m, p, R$^2$, R$^3$, R$^4$, R$^5$, and R$^6$ are as defined above. Preferably, R$^2$, R$^3$, R$^4$, R$^5$, and R$^6$ are independently selected from the group consisting of C$_1$-C$_6$ alkyl or phenyl.

Examples of solvents for this reaction include organic, protic, or aqueous solvents which are inert under the reaction conditions, such as: aromatic hydrocarbons, chlorinated hydrocarbons, ethers, aliphatic hydrocarbons, alcohols, water, or mixtures thereof. Preferred solvents include benzene, toluene, p-xylene, methylene chloride, dichloroethane, dichlorobenzene, tetrahydrofuran, diethylether, pentane, methanol, ethanol, water, or mixtures thereof. More preferably, the solvent is benzene, toluene, p-xylene, methylene chloride, dichloroethane, dichlorobenzene, tetrahydrofuran, diethylether, pentane, methanol, ethanol, or mixtures thereof.

A suitable temperature range is from about $-20°$ C. to about 125° C., preferably 35° C. to 90° C., and more preferably 50° C. to 65° C. Pressure is not critical but may depend on the boiling point of the solvent used, i.e., use sufficient pressure to maintain a solvent liquid phase. Reaction times are not critical, and can be from several minutes to 48 hours. The reactions are generally carried out in an inert atmosphere, most preferably nitrogen or argon.

The reaction is usually carried out by dissolving the compound (XX$_1$ML$_n$L$^1$$_m$)$_p$ in a suitable solvent, adding the cyclopropene (preferably in a solvent) to a stirred solution of the compound, and optionally heating the mixture until the reaction is complete. The progress of the reaction can be monitored by any of several standard analytical techniques, such as infrared or nuclear magnetic resonance. Isolation of the product can be accomplished by standard procedures, such as evaporating the solvent, washing the solids (e.g., with alcohol or benzene), and then recrystallizing the desired carbene complex. Whether the moieties X, X$^1$, L, or L$^1$ are (unidentare) ligands or some taken together to form multidentate ligands will depend on the starting compound which simply carries these ligands over into the desired carbene complex.

In one variation of this general procedure, the reaction is conducted in the presence of HgCl$_2$, preferably 0.01 to 0.2 molar equivalents, more preferably 0.05 to 0.1 equivalents, based on XX$^1$ML$_n$L$^1$$_m$. In this variation, the reaction temperature is preferably 15° C. to 65° C.

In a second variation of the general procedure, the reaction is conducted in the presence of ultraviolet radiation. In this variation, the reaction temperature is preferably −20° C. to 30° C.

It is also possible to prepare carbene complexes of this invention by ligand exchange. For example, L and/or $L^1$ can be replaced by a neutral electron donor, $L^2$, in compounds of Formula I by reacting $L^2$ with compounds of Formula I wherein L, $L^1$, and $L^2$ are independently selected from phosphine, sulfonated phosphine, phosphite, phosphinite, phosphonite, arsine, stibine, ether, amine, amide, sulfoxide, carbonyl, nitrosyl, pyridine or thioether. Similarly, X and/or $X^1$ can be replaced by an anionic ligand, Y, in compounds of Formula I by reacting $M^1Y$ with compounds of Formula I, wherein X and $X^1$ are independently selected from halogen, hydrogen, or $C_1$–$C_{20}$ alkyl, aryl, $C_1$–$C_{20}$ alkoxide, aryloxide, $C_2$–$C_{20}$ alkoxycarbonyl, arylcarboxylate, $C_1$–$C_{20}$ carboxylate, aryl or $C_1$–$C_{20}$ alkylsulfonate, $C_1$–$C_{20}$ alkylthio, $C_1$–$C_{20}$ alkylsulfonyl, $C_1$–$C_{20}$ alkylsulfinyl, each optionally substituted with $C_1$–$C_5$ alkyl, halogen, $C_1$–$C_5$ alkoxy or with a phenyl group optionally substituted with halogen, $C_1$–$C_5$ alkyl or $C_1$–$C_5$ alkoxy. These ligand exchange reactions are typically carried out in a solvent which is inert under the reaction conditions. Examples of solvents include those described above for the preparation of the carbene complex.

The compounds of this invention are useful as catalysts in the preparation of a wide variety of polymers which can be formed by ring-opening metathesis polymerization of cyclic olefins. Therefore, one embodiment of this invention is an improved polymerization process comprising metathesis polymerization of a cyclic olefin, wherein the improvement comprises conducting the polymerization in the presence of a catalytic amount of a compound of Formula I. The polymerization reaction is exemplified for norbornene in the following equation:

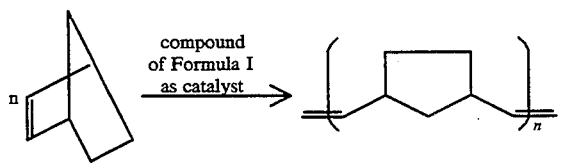

wherein n is the repeat unit of the polymeric chain.

Examples of cyclic olefins for this polymerization process include norbornene, norbornadiene, cyclopentene, dicyclopentadiene, cycloheptene, cyclo-octene, 7-oxanorbornene, 7-oxanorbornadiene, and cyclododecene.

The polymerization reaction is generally carried out in an inert atmosphere by dissolving a catalytic amount of a compound of Formula I in a solvent and adding the cyclic olefin, optionally dissolved in a solvent, to the catalyst solution. Preferably, the reaction is agitated (e.g., stirred). The progress of the reaction can be monitored by standard techniques, e.g., nuclear magnetic resonance spectroscopy.

Examples of solvents for the polymerization reaction include organic, protic, or aqueous solvents which are inert under the polymerization conditions, such as: aromatic hydrocarbons, chlorinated hydrocarbons, ethers, aliphatic hydrocarbons, alcohols, water, or mixtures thereof. Preferred solvents include benzene, toluene, p-xylene, methylene chloride, dichloroethane, dichlorobenzene, tetrahydrofuran, diethylether, pentane, methanol, ethanol, water, or mixtures thereof. More preferably, the solvent is benzene, toluene, p-xylene, methylene chloride, dichloroethane, dichlorobenzene, tetrahydrofuran, diethylether, pentane, methanol, ethanol, or mixtures thereof. Most preferably, the solvent is toluene or a mixture of benzene and methylene chloride. The solubility of the polymer formed in the polymerization reaction will depend on the choice of solvent and the molecular weight of the polymer obtained.

Reaction temperatures can range from 0° C. to 100° C., and are preferably 25° C. to 45° C. The ratio of catalyst to olefin is not critical, and can range from 1:5 to 1:10,000, preferably 1:10 to 1:1,000.

Because the compounds of Formula I are stable in the presence of protic solvents, the polymerization reaction may also be conducted in the presence of a protic solvent. This is very unusual among metathesis catalysts and provides a distinct advantage for the process of this invention over the processes of the prior art. Other advantages of the polymerization process of this invention derive from the fact that the compounds of Formula I are well-defined, stable Ru or Os carbene complexes providing high catalytic activity. Using such compounds as catalysts allows control of the rate of initiation, extent of initiation, and the amount of catalyst. Also, the well-defined ligand environment of these complexes provides flexibility in modifying and fine-tuning their activity level, solubility, and stability. In addition, these modifications enable ease of recovery of catalyst.

General Description of the Preparation of Compounds of this Invention from Cyclopropenes:

A 50 ml Schlenk flask equipped with a magnetic stirbar is charged with $(MXX^1L_nL^1m)_p$ (0.1 mmol) inside a nitrogen-filled drybox. Methylene chloride (2 ml) is added to dissolve the complex followed by 25 ml of benzene to dilute the solution. One equivalent of a cyclopropene is then added to this solution. The reaction flask is then capped with a stopper, removed from the box, attached to a reflux condenser under argon and heated at 55° C. The reaction is then monitored by NMR spectroscopy until all the reactants have been converted to product. At the end of the reaction, the solution is allowed to cool to room temperature under argon and then filtered into another Schlenk flask via a cannula filter. All solvent is then removed in vacuo to give a solid. This solid is then washed with a solvent in which the by-product will be soluble but the desired product will not. After the washing supernatant is removed, the resulting solid powder is dried in vacuo overnight. Further purification via crystallization can be performed if necessary.

The abbreviations Me, Ph, and THF used herein refer to methyl, phenyl, and tetrahydrofuran, respectively.

Representative compounds of the present invention which are prepared in accordance with the procedure described above are exemplified in Table I.

TABLE I $$\begin{array}{c} X \quad L \quad R \\ \diagdown \mid \diagup \\ M=C \\ \diagup \mid \diagdown \\ X^1 \quad L^1 \quad R^1 \end{array}$$

| Compound Name | M | X | $X^1$ | L | $L^1$ | R | $R^1$ |
|---|---|---|---|---|---|---|---|
| Dichloro-3,3-diphenylvinyl-carbene-bis(triphenylphosphine)ruthenium(II) | Ru | Cl | Cl | $PPh_3$ | $PPh_3$ | H | $CH=CPH_2$ |
| Dibromo-3,3-diphenylvinyl-carbene-bis(triphenylphosphine)ruthenium(II) | Ru | Br | Br | $PPh_3$ | $PPh_3$ | H | $CH=CPh_2$ |
| Dichloro-3,3-diphenylvinyl-carbene-bis(methyldiphenylphosphine)ruthenium(II) | Ru | Cl | Cl | $PPh_2Me$ | $PPh_2Me$ | H | $CH=CPh_2$ |
| Dibromo-3,3-diphenylvinyl-carbene-bis(methyldiphenylphosphine)ruthenium(II) | Ru | Br | Br | $PPh_2Me$ | $PPh_2Me$ | H | $CH=CPH_2$ |
| Dichloro-3-methyl-3-phenylvinylcarbene-bis(triphenylphosphine)-ruthenium(II) | Ru | Cl | Cl | $PPh_3$ | $PPh_3$ | H | CH=C(Me)(Ph) |
| Dibromo-3-methyl-3-phenylvinylcarbene-bis(triphenylphosphine)-ruthenium(II) | Ru | Br | Br | $PPh_3$ | $PPh_3$ | H | CH=C(Me)(Ph) |
| Dichloro-3,3-dimethyl-vinylcarbene-bis(triphenylphosphine)ruthenium(II) | Ru | Cl | Cl | $PPh_3$ | $PPh_3$ | H | CH=C(Me)(Me) |
| Bis(acetato)-3,3-diphenyl-vinylcarbene-bis(triphenylphosphine)ruthenium(II) | Ru | O=C(OMe) | O=C(OMe) | $PPh_3$ | $PPh_3$ | H | CH=C(Ph)(Ph) |
| Acetato-3,3-diphenylphosphine)ruthenium(II)-chloride | Ru | O=C(OMe) | Cl | $PPh_3$ | $PPh_3$ | H | CH=C(Ph)(Ph) |
| 3,3-Diphenylvinylcarbene-bis(trifluoroacetato)bis-(triphenylphosphine)-ruthenium(II) | Ru | O=C(OCF_3) | O=C(OCF_3) | $PPh_3$ | $PPh_3$ | H | CH=C(Ph)(Ph) |
| 3,3-Diphenylvinylcarbene-$n^2$-pinacol-bis(triphenylphosphine)ruthenium(II) | Ru | Me_2C(O)– | –C(Me)_2O | $PPh_3$ | $PPh_3$ | H | CH=C(Ph)(Ph) |
| 3,3-Diphenylvinylcarbene-bis(t-butoxy)bis-(triphenylphosphine ruthenium-(II) | Ru | $Me_3CO$ | $Me_3CO$ | $PPh_3$ | $PPh_3$ | H | CH=C(Ph)(Ph) |
| 3,3-Diphenylvinylcarbene-bis(2-trifluoromethyl-2-propoxy)-bis(triphenylphosphine)ruthenium(II) | Ru | (Me)(F_3C)(Me)CO | (Me)(F_3C)(Me)CO | $PPh_3$ | $PPh_3$ | H | CH=C(Ph)(Ph) |

These are representative examples of the ruthenium complexes. Analogous complexes could be made with osmium.

EXAMPLE I

Synthesis of

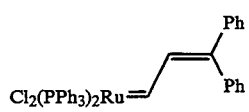

In a typical reaction, a 200 ml Schlenk flask equipped with a magnetic stirbar was charged with RuCl_2(PPh_3)_4 (6.00 g, 4.91 mmol) inside a nitrogen-filled drybox. Methylene chloride (40 mL) was added to dissolve the complex followed by 100 mL of benzene to dilute the solution. 3,3-Diphenylcyclopropene (954 mg, 1.01 equiv) was then added to the solution via pipette. The reaction flask was capped with a stopper, removed from the box, attached to a reflux condenser under argon and heated at 53° C. for 11 h. After allowing the solution to cool to room temperature, all the solvent was removed in vacuo to give a dark yellow-brown solid. Benzene (10 mL) was added to the solid and subsequent swirling of the mixture broke the solid into a fine powder. Pentane (80 mL) was then slowly added to the mixture via cannula while stirring vigorously. The mixture was stirred at room temperature for 1 h and allowed to settle before the supernatant was removed via cannula filtration. This washing procedure was repeated two more times to ensure the complete removal of all phosphine by-products. The resulting solid was then dried under vacuum overnight to afford 4.28 g (98%) of Compound 1 as a yellow powder with a slight green tint. $^1$H NMR (C$_6$D$_6$): $\delta$17.94 (pseudo-quartet= two overlapping triplets, 1H, Ru=CH, $J_{HH}$=10.2 Hz, $J_{PH}$=9.7 Hz), 8.33(d, 1H, CH=CPh$_2$, $J_{HH}$ 10.2 Hz). $^{31}$P NMR (C$_6$D$_6$): $\delta$28.2 (s). $^{13}$C NMR(CD$_2$Cl$_2$): $\delta$288.9 (t, M=C, $J_{CP}$=10.4 Hz), 149.9 (t, CH=CPh$_2$, $J_{CP}$=11.58 Hz).

The carbene complex which is the compound formed in the above example is stable in the presence of water or alcohol.

EXAMPLE II

Synthesis procedure for

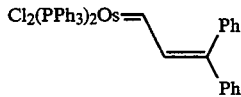
2

A 50 ml Schlenk flask equipped with a magnetic stirbar was charged with OsCl$_2$(PPh3)$_3$ (100 mg, 0.095 mmol) inside a nitrogen-filled drybox. Methylene chloride (2 ml) was added to dissolve the complex followed by 25 ml of benzene to dilute the solution. 3,3-diphenyl-cyclopropene (18.53 mg, 1.01 eq) was then added to the solution via piper. The reaction flask was capped with a stopper, removed from the box, attached to a reflux condenser under argon and heated at 55° C. for 14 h. After allowing the solution to cool to room temperature, all the solvent was removed in vacuo to give a dark yellow-brown solid. Benzene (2 ml) was added to the solid and subsequent swirling of the mixture broke the solid into a fine powder. Pentane (30 ml) was then slowly added to the mixture via cannula while stirring vigorously. The mixture was stirred at RT for 1 h and allowed to settle before the supernatant was removed via cannula filtration. This washing procedure was repeated two more times to ensure the complete removal of all phosphine by-products. The resulting solid was then dried under vacuum overnight to afford 74.7 mg of Compound 2 as a yellow powder (80%). $^1$H NMR (C$_6$D$_6$): $\delta$19.89 (pseudo-quartet=two overlapping triplets, 1H, Os=CH, $J_{HH}$=10.2 Hz), 8.23 (d, 1H, CH=CPh$_2$, $J_{HH}$=10.2 Hz). $^{31}$P NMR (C$_6$D$_6$): $\delta$4.98 (s).

EXAMPLE III

Synthesis of

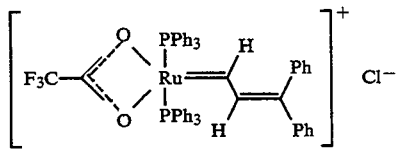
3

A 50 ml Schlenk flask equipped with a magnetic stirbar was charged with RuCl$_2$(PPh$_3$)$_2$(=CH-CH=CPPh$_2$) (100 mg, 0.18 mmol) inside a nitrogen-filled drybox. Methylene chloride (10 ml) was added to dissolve the complex. AgCF$_3$CO$_2$(24.9 mg., 1 eq) was weighed into a 10 ml round-bottom flask, dissolved with 3 ml of THF. Both flasks were then capped with rubber septa and removed from the box. The Schlenk flask was then put under an argon atmosphere and the AgCF$_3$CO$_2$ solution was added dropwise to this solution via a gas-tight syringe over a period of 5 min while stirring. At the end of the addition, there was a lot of precipitate in the reaction mixture and the solution turned into a fluorescent green color. The supernatant was transferred into another 50 ml Schlenk flask under argon atmosphere via the use of a cannula filter. Subsequent solvent removal under in vacuo and washing with pentane (10 ml) afforded a green solid powder, Compound 3. Yield=92.4 mg (85%). $^1$H NMR (2:2:1 CD$_2$Cl$_2$:C$_6$D$_6$:THF-d$_8$) :$\delta$18.77 (dt, 1H, Ru=CH, $J_{HH}$=11.2 Hz, $J_{PH}$=8.6 Hz), 8.40 (d, 1H), CH=CPh$_2$, $J_{HH}$=11.2 Hz). $^{31}$P NMR (2:2:1 CD$_2$Cl$_2$: C$_6$D$_6$:THF-d$_8$)$\delta$29.4. $^{19}$F NMR (2:2:1 CD$_2$Cl$_2$:C$_6$D$_6$:THF-d$_8$) $\delta$75.8.

EXAMPLE IV

Synthesis of

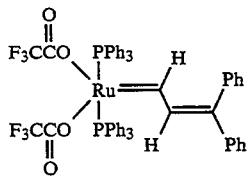
4

A 50 ml Schlenk flask equipped with a magnetic stirbar was charged with RuCl$_2$(PPh$_3$)$_2$(= CH—CH=CPh$_2$) (100 mg, 0.11 mmol) inside a nitrogen-filled drybox. Methylene chloride (10 ml) was added to dissolve the complex. AgCF$_3$CO$_2$ (49.8 mg, 2 eq) was weighed into a 10 ml round-bottom flask, dissolved with 4 ml of THF. Both flasks were then capped with rubber septa and removed from the box. The Schlenk flask was then put under an argon atmosphere and the AgCF$_3$CO$_2$ solution was added dropwise via a gas tight syringe over a period of 5 min to the solution of ruthenium compound while stirring. At the end of the addition, there was a lot of precipitate in the reaction mixture and the solution turned into a fluorescent lime green color. The supernatant was transferred into another 50 ml Schlenk flask under argon atmosphere with the use of a cannula filter. Subsequent solvent removal in vacuo and washing with pentane (10 ml) afforded a green powder, Compound 4. Yield = 102 mg (87%). $^1$H NMR (2:2:1 CD$_2$Cl$_2$:C$_6$D$_6$:THF-d$_8$) $\delta$19.23 (dt, slightly overlapping) Ru=CH, $J_{HH}$=11.5 Hz, $J_{PH}$=5.4 Hz), 8.07 (d, 1H, CH=CPH$_2$, $J_{HH}$11.5 Hz). $^{31}$P NMR (2:2:1 CD$_2$Cl$_2$:C$_6$D$_6$:THF-d$_8$) $\delta$28.6. $^{19}$F NMR (2:2:1 CD$_2$Cl$_2$:C$_6$D$_6$:THF-d$_8$) $\delta$−75.7.

EXAMPLE V

Synthesis of

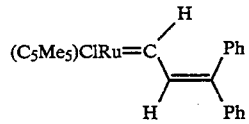
5

The reaction between [Ru(C$_5$Me$_5$)Cl]$_4$ and 3,3-diphenylcyclopropene was done under a nitrogen atmosphere. [Ru(C$_5$Me$_5$)Cl]$_4$ (100 mg, 0.092 mmoL) was dissolved in 10 mL of tetrahydrofuran. To this solution was added 3,3-diphenylcyclopropene (350 rag, 1.82 mmoL). The resulting solution was stirred at room temperature for 1 h. Petroleum ether (10 mL) was then added to the reaction mixture. It was stirred for an additional 30 min, and then all volatile components were removed from the reaction mixture under vacuum. The crude product was extracted with diethyl ether; volatiles were removed from the filtrate under vacuum to afford a dark colored, oily solid. This was further extracted with petroleum ether; volatiles were removed from the filtrate under vacuum to afford a very dark red-brown oil. This was recrystallized from petroleum ether at −40° C. to afford dark crystals. NMR spectra of which are consistent with the formulation $[Ru(C_5Me_5)(CHC=CPh_2)Cl]_n$ (value of n as yet undetermined: e.g., the product could be a dimer).

EXAMPLE VI

Polymerization of Norbornene Using Compound of Example 1

$(PPh_3)_2Cl_2Ru=CH—CH=CPh_2$ catalyzed polymerized norbornene in a 1.8 mixture of $CH_2Cl_2/C_6H_6$ at room temperature to yield polynorbornene. A new signal, attributed to $H_\alpha$ of the propagating carbene, was observed by $^1H$ NMR spectroscopy at 17.79 ppm. Its identity and stability was confirmed by preparing a block polymer with 2,3-dideuteronorbornene and perprotionorbornene. When 2,3-dideuteronorbornene was added to the propagating species,, the new carbene signal vanished and then reappeared when perprotionorbornene was added for the third block.

EXAMPLE VII

Polymerization of Norbornene Using Compound of Example 5

$Ru(C_5Me_5)(CHC=CPh_2)Cl$ (14 mg, 0.030 mmoL) was dissolved in 1 mL of perdeuterated toluene under a nitrogen atmosphere. To this was added norbornene (109 mg, 1.16 mmoL). The reaction mixture became viscous within minutes as the norbornene polymerized. After 20 hrs at room temperature a $^1H$ NMR spectrum of the reaction mixture was recorded, which showed polynorbornene and unreacted norbornene monomer in a ratio of 82:12.

What is claimed is:

1. In the process of metathesis polymerization of cyclic olefins, the improvement comprising carrying out the polymerization in the presence of a catalyst of the formula

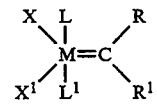

in the presence of a solvent, wherein:

M is Os or Ru;

R and $R^1$ are independently selected from hydrogen; $C_1-C_{20}$ alkyl, $C_2-C_{20}$ alkenyl, $C_2-C_{20}$ alkynyl, $C_2-C_{20}$ alkoxycarbonyl, aryl, $C_1-C_{20}$ carboxylate, $C_1-C_{20}$ alkoxy, $C_2-C_{20}$ alkenyloxy, $C_2-C_{20}$ alkynyloxy or aryloxy; each optionally substituted with $C_1-C_5$ alkyl, halogen, $C_1-C_6$ alkoxy or with a phenyl group substituted with halogen, $C_1-C_5$ alkyl or $C_1-C_5$ alkoxy;

X and $X^1$ are independently selected from an anionic ligand; and

L and $L^1$ are independently selected from neutral electron donor.

2. In the process of claim 1, wherein the cyclic olefin is norbornene, norbornadiene, cyclopentene, dicyclopentadiene, cycloheptene, cyclo-octene, 7-oxanorbornene, 7-oxanorbornadiene, or cyclododecene.

3. A process according to claim 1 wherein the catalyst is dissolved in a protic, aqueous or organic solvent or mixture thereof.

4. A process according to claim 1 wherein 2,3 or 4 of X, $X^1$, L and, $L^1$ are bonded together to create a chelating multidentate ligand.

5. A process according to claim 4 wherein X, L and $L^1$ are taken together to be cyclopentadienyl, indenyl or fluorenyl therefor; each optionally substituted with hydrogen, $C_2-C_{20}$ alkenyl, $C_2-C_{20}$ alkynyl, $C_1-C_{20}$ alkyl, aryl, $C_1-C_{20}$ carboxylate, $C_1-C_{20}$ alkoxy, $C_2-C_{20}$ alkenyloxy, $C_2-C_{20}$ alkynyloxy, aryloxy, $C_2-C_{20}$ alkoxycarbonyl, $C_1-C_{20}$ alkylthio, $C_1-C_{20}$ alkylsulfonyl or $C_1-C_{20}$ alkylsulfinyl; each optionally substituted with $C_1-C_5$ alkyl, halogen, $C_1-C_5$ alkoxy or with a phenyl group optionally substituted with halogen, $C_1-C_5$ alkyl or $C_1-C_5$ alkoxy.

* * * * *

UNITED STATES PATENT AND TRADEMARK OFFICE
CERTIFICATE OF CORRECTION

PATENT NO. : 5,342,909
DATED : August 30, 1994
INVENTOR(S) : Robert H. Grubbs, et al It is certified that error appears in the above-indentified patent and that said Letters Patent is hereby corrected as shown below:

Column 1, line 5, after the title add the following:

-- ORIGIN OF INVENTION
The U.S. Government has certain rights in this invention pursuant to Grant No. CHE 8922072 awarded by the National Science Foundation.--

Signed and Sealed this

Fifth Day of March, 1996

Attest:

BRUCE LEHMAN

Attesting Officer

Commissioner of Patents and Trademarks